(12) United States Patent
Markart et al.

(10) Patent No.: US 6,524,845 B1
(45) Date of Patent: Feb. 25, 2003

(54) APPARATUS FOR THE DETERMINATION OF MICROORGANISMS IN LIQUID TEST SPECIMENS

(75) Inventors: Ernst Markart, Munich (DE); Michael Voigt, Munich (DE); Genrich Siris, Munich (DE); Klaus Deuter, Unterschleissheim (DE)

(73) Assignee: LRE Technology Partner GmbH, Munich (DE)

( * ) Notice: Subject to any disclaimer, the term of this patent is extended or adjusted under 35 U.S.C. 154(b) by 203 days.

(21) Appl. No.: 09/714,462

(22) Filed: Nov. 16, 2000

(30) Foreign Application Priority Data

Nov. 17, 1999 (DE) .......................... 199 55 372

(51) Int. Cl.⁷ .............................. C12M 1/34
(52) U.S. Cl. ................ 435/287.3; 435/286.4; 435/287.4; 435/288.7; 422/65
(58) Field of Search .................. 422/65, 82.05; 435/286.2, 286.4, 287.3, 287.4, 288.4, 288.7, 303.1, 808

(56) References Cited

U.S. PATENT DOCUMENTS

| | | | | |
|---|---|---|---|---|
| 3,772,154 A | * | 11/1973 | Isenberg et al. ......... | 435/286.4 |
| 4,116,775 A | * | 9/1978 | Charles et al. ............... | 356/246 |
| 4,676,951 A | * | 6/1987 | Armes et al. ................ | 222/136 |
| 4,800,164 A | * | 1/1989 | Bisconte ................... | 435/286.4 |
| 5,573,950 A | * | 11/1996 | Graessle et al. ............. | 422/104 |
| 5,646,049 A | * | 7/1997 | Tayi ............................. | 422/63 |
| 5,863,754 A | * | 1/1999 | Bajard .......................... | 422/63 |
| 6,132,685 A | * | 10/2000 | Kercso et al. ............... | 422/104 |

* cited by examiner

Primary Examiner—David A. Redding
(74) Attorney, Agent, or Firm—McCormick, Paulding & Huber LLP

(57) ABSTRACT

An apparatus for determining microorganisms in liquid test specimens includes a specimen providing station (10) with a transport apparatus (32, 36) for the continuous provision of cuvettes (26) containing specimens to be investigated, a dosing station (12) with a pipetting apparatus (14) for removing specimens from cuvettes (26) and for filling the specimens into measuring chambers formed in a measuring chamber plate (86) in matrix arrangement, a measuring station (16) with a measuring apparatus (146) for optically measuring the specimens in the measuring chambers and an endless conveyor (18) for serially receiving the measuring chamber plates (86) and for transporting the same through a dosing station (12), a measuring station (16) and through a temperature controllable waiting zone (22).

44 Claims, 8 Drawing Sheets

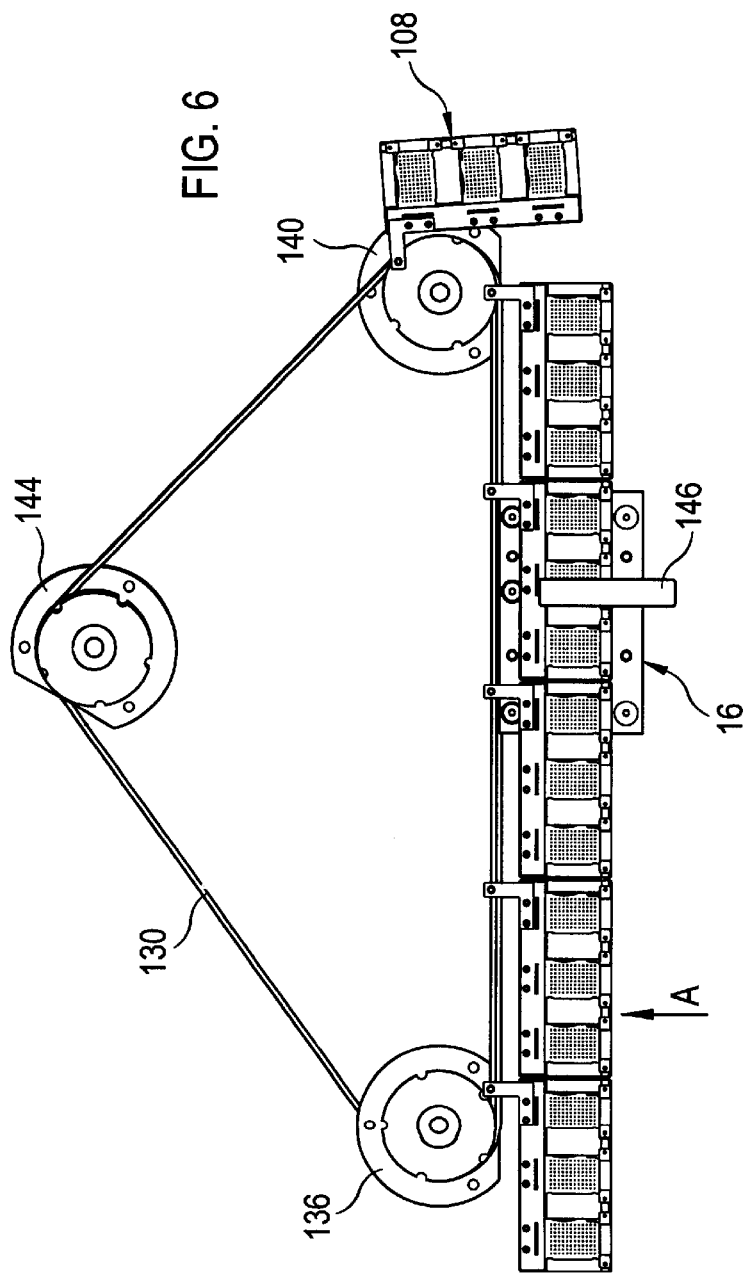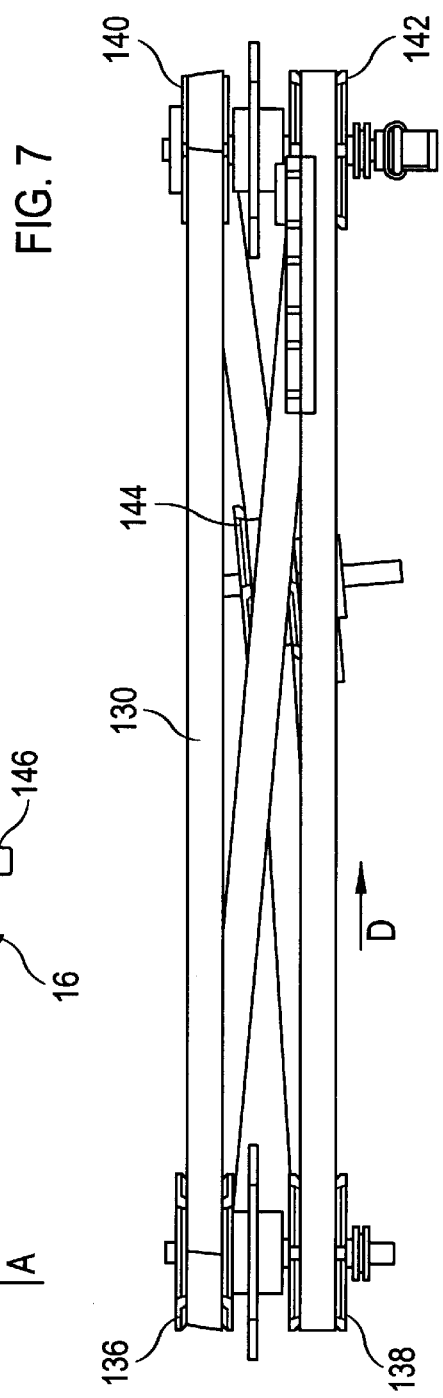

APPARATUS FOR THE DETERMINATION OF MICROORGANISMS IN LIQUID TEST SPECIMENS

FIELD OF THE INVENTION

The invention concerns an apparatus for the determination of microorganisms in liquid test specimens, including a specimen providing station with a transport apparatus for the continuous presentation of cuvettes containing specimens to be investigated, a dosing station with a pipetting apparatus for removing specimens from the cuvettes and for filling the specimens into measuring chambers formed in a measuring chamber plate in matrix arrangement, and a measuring station with a measuring apparatus for optically measuring the specimens in the measuring chambers.

BACKGROUND OF THE INVENTION

In order to be able to detect, for example, bacteria in liquid test specimens with an apparatus of the previously mentioned kind, one proceeds as follows. The measuring chambers of the measuring chamber plate, a so-called microtitration plate, are filled with a culturing solution and/or detection chemicals for certain bacteria. A specimen is distributed to a number of chambers. With the help of the measuring device, it is tested whether the absorption behavior of the solution in the measuring chambers changes, especially whether a color reaction appears because of the detection chemicals. If this is not the case, the measuring chamber plate is placed in an oven to produce a multiplication of the bacteria in the individual measuring chambers. The above-mentioned steps must be repeated many times during a time period of from six to eight hours. This means that the measuring chamber plate has to be taken out of the oven by means of a grasping system and moved to the dosing unit, the measuring unit, and finally back into the oven. This is time consuming and requires not only a high mechanical expense but also much space for the storage of the measuring chamber plates. If an error appears in the mechanical handling which is not immediately noted, the process because of its long duration often cannot be started again until the next work day.

The invention has as its object, to simplify the manipulation of the measuring chamber plates and thereby to avoid sources of error, as well as to reduce the space requirement of the apparatus.

SUMMARY OF THE INVENTION

These objects are solved by an apparatus of the previously mentioned kind and in accordance with the invention by an endless conveyor which is formed to serially receive the measuring chamber plates and to transport the same through the dosing station, the measuring station and through a temperature controllable waiting zone.

In the solution of the invention, the measuring chamber plates remain connected with the endless conveyor during the entire duration of the investigation. The grasping apparatus required by the state of the art for the manipulation of the measuring chamber plates can be eliminated. Thus, the technical expense is lowered and also so is the space requirement for the apparatus of the invention. Since the previously required manipulation procedure offered an abundance of error sources, the apparatus of the invention in operation is also essentially more functionally reliable than customary apparatuses of this kind.

Preferably, the endless conveyor has a plurality of carrier frames each having at least one receiving compartment for a measuring chamber plate. Therefore, the measuring chamber plates can in a simple way be connected with the endless conveyor, insofar as each is simply inserted or pushed into a receiving compartment.

The endless conveyor preferably has an endless conveying member, for example, a belt or chain, which is guided over rolls and to which the carrier frames are fastened. To save space, or with the same space allotment to increase the storage capacity for the measuring chamber plates, the conveyor member can run in at least two vertically superimposed planes. This can be achieved in a simple way in that at two horizontally spaced locations at least two belt rolls are arranged axially over one another, and that at least a further direction changing roll is provided for the conveyor member which has a location outside of a connecting line between the first mentioned belt roll locations. In this way, the carrier frames fastened to the conveyor member can change from one plane to the other without obstructing one another.

The use of so-called microtitration plates in which the measuring chambers each have a very small volume requires an exact positioning of the measuring chamber plates in the optical measuring apparatus. To achieve this, it is advantageous if guide means are provided at the measuring station for guiding the carrier frames relative to the measuring apparatus. Thereby the measuring chamber plates can be positioned exactly with respect to the measuring optic system despite the flexibility of the conveyor member.

In a preferred embodiment the guide means include guide rolls arranged on both sides of the transport path of the carrier frames and which come into engagement with the side edges of the carrier frames running parallel to the transport direction. To on one hand make possible a jolt-free introduction of the carrier frames between the guide rolls and on the other hand to assure an exact positioning, it is advantageous if the guide roll intended for engagement with one of the side faces is biased in the direction toward to the oppositely lying guide roll. Thereby a play-free engagement of the guide rolls onto the side surfaces of the carrier frame is assured.

In order to avoid not only sideways deflection but also movement of the measuring chamber plates in the vertical direction inside of the measuring station, it is proposed that guide grooves are formed in the side surfaces of the carrier frames running parallel to the transport direction, which grooves receive corresponding portions of the guide rolls. The centering of the carrier frames at the measuring station can, in this case, be further improved if the guide grooves and/or the guide rolls in their edge areas have a V-profile.

The receiving compartment of the carrier frame is preferably formed as a sliding guide with an opening lying at the side of the carrier frame remote from the conveyor member. Because of this, the measuring chamber plates can be pushed into the associated receiving compartments by a simple pushing mechanism at the dosing station and can also be likewise easily removed.

Since the measuring chamber plates remain in the carrier frames during the entire investigation procedure and are also measured while in the carrier frames, it is advantageous if the carrier frames either have entirely no bottoms or if the bottom of the receiving compartment at least in the region of the measuring chambers of a measuring chamber plate inserted into the receiving compartment is transparent. This can occur either in that a transparent plate is so printed that measuring areas only remain free at the desired spots or in that the bottom of the receiving compartment at the spots corresponding to the measuring chambers of a measuring chamber plate inserted into the measuring compartment has passthrough openings.

To simplify the automatic delivery of the measuring chamber plates for the inoculation, it is advantageous if at the dosing station, at least one magazine pocket is provided for the storage of measuring chamber plates stacked upon one another and if a delivery device is also provided for delivering the uppermost or lowermost measuring chamber plate of the stack from the magazine pocket to a receiving compartment of a carrier frame moving past the dosing station. Also, in the case of this solution, no complicated grasping system is needed. It is sufficient to have a simple pusher for removing the measuring chamber plate from the magazine. If the magazine pocket is located below the delivery surface for the insertion of a measuring chamber plate into a receiving compartment, it is advantageous if, in the magazine pocket, an upwardly biased bottom plate is arranged so that the entire measuring chamber plate stack is always pushed against an upper stop.

The delivery mechanism for delivery of the measuring chamber plates is preferably so formed and controlled that a measuring chamber plate removed from the magazine pocket is positioned at a dosing position at which the specimen material is filled into the measuring chambers and subsequently, the measuring chamber plate is delivered to the receiving compartment of a carrier frame. This positioning movement can be carried out by one simple pusher.

Since one and the same specimen as a rule is investigated in respect to different bacteria, in the measuring plate at least one group of measuring chambers is formed which are connected with at least one filling opening and with one another by capillaries. This gives the possibility of filling all of the measuring chambers with one single filling procedure. The filling opening for this simple filling can be formed relatively large. The measuring chambers, however, need to have only very small volumes. This reduces not only the space requirement for the individual measuring chamber plates, but reduces above all also the volume of specimen that has to be supplied and also after the completion of the investigation, of the appearing waste which often has to be taken care of as special waste.

Preferably, in each measuring chamber plate, the measuring chambers are arranged in rows and columns with the measuring chambers lying in one row being connected by capillaries and with the filling openings of the rows being arranged in a column. This again simplifies the automatic filling of the specimens by means of the pipetting apparatus.

Preferably the column of filling openings is arranged at an end of the measuring chamber plate with respect to the insertion direction and extends perpendicularly to the insertion direction, with the carrier frame being provided with a cover which closes the filling openings of a measuring chamber plate inserted into a receiving compartment. Thereby since the measuring chambers as well as the filling openings are covered, it is assured that during the movement of the measuring chamber plates by the endless conveyor no material can be deflected out of the measuring chambers nor can any foreign material get into the measuring chambers.

To assure that the specimen liquid also arrives into the last measuring chamber of a measuring chamber row, it is advantageous if at the end of a row of connected together measuring chambers, an air receiving hollow space is arranged.

To be able to achieve the reception in all of the measuring chambers of exactly the same amount of liquid, in the capillary between each two measuring chambers a cross-sectional change is formed which prevents the automatic passage of liquid by capillary effect and which prevention of capillary effect can be removed by exerting an externally generated effect onto the measuring chamber plate. If, for example, each of the measuring chambers are only to be half filled, it must be assured that the filled in liquid does not first arrive at the last measuring chamber of the measuring chamber row and entirely fill that chamber which would be the case with an unhindered fluid passage through the capillaries. With the previously described solution, the desired amount arrives first only up to the cross-sectional change. It is then allowed to flow further by the external effect exerted on the measuring chamber plate and so forth until the last chamber has been reached. In this way, the measuring chambers are filled one after the other with the desired amount, without one of these chambers being entirely filled while the others remain empty. One possibility for exerting an effect on the measuring chamber plates in the desired way exists, for example, in that an ultrasonic driver is arranged at the dosing station which is couplable with the measuring chamber plate. By an appropriate ultrasonic impulse, the liquid at the cross-sectional change of a capillary is induced to overcome the "block" and to flow further under the effect of the capillary force.

A measuring chamber plate of the previously described kind can be made in a very simple way in that the measuring chambers and the capillaries are formed by upwardly open recesses in the measuring chamber plates and are subsequently closed by a cover foil. This cover foil is for the optical measurement transparent at least in the area of the measuring chambers.

Also, the measuring chamber plate is advantageously transparent at least in the region of the measuring chamber bottoms and moreover is preferably made of an opaque material to inhibit stray light from one measuring chamber reaching another measuring chamber. A sufficient optical transparency can, therefore, be achieved in that the measuring chamber bottoms have a small thickness in comparison to the thickness of the plate so that the measuring chamber plate is opaque except for at the measuring chamber bottoms.

To inhibit the effect of stray light in the measurement of the measuring chambers and also to enable the use of small or weak light sources, at least one side of each measuring chamber bottom can be formed as a light refracting surface; for example, as a convex lens.

So that the measuring apparatus need not individually sense the measuring chambers of a connected measuring chamber row, it is advantageous if a plurality of pairs of light transmitters/light sensors are provided which pairs in number and arrangement correspond to the measuring chambers of at least one measuring chamber row.

The liquids to be investigated are mostly delivered in cuvettes, which for example are arranged eight at a time in elongated rectangular shaped cuvette holders or racks. The test specimen providing station in accordance with the inventive solution has a cuvette receiving location and a cuvette take-off location in which the cuvette holders are transported perpendicularly to their longitudinal directions, and which locations are connected by a longitudinal conveyor through which the cuvette holders are transported past the dosing station. With the help of the pipetting apparatus, the specimens can be removed from the cuvettes and distributed to the measuring chamber plates. To effect the transfer of the cuvette holders from perpendicular movement to longitudinal movement with the lowest possible technical expense, the inventive solution uses for the longitudinal conveyor an endless conveyor belt which at each end of the longitudinal conveyor is trained over a belt roll and which is receivable in a slot, parallel to the belt direction, in a support surface flush with the transport plane at the cuvette receiving location and the cuvette take-off location, and each of which rolls at a part of its circumferences is flattened along a circular secant. At their flattened regions, the belt rolls do not extend above the support surface so that in the position of a belt roll in which its flattening is located below the underside of the support surface no contact exists between the conveyor belt and the underside of the cuvette holder standing on the support surface. This means that in this position of the belt roll a cuvette holder can be pushed onto and pushed off of the support surface. If the belt roll rotates further, the section of the belt roll having full radius extends through the slot in the support surface so that the conveyor belt comes into contact with the underside of a cuvette holder standing on the support surface and moves the cuvette holder in the longitudinal direction of the conveyor. This solution makes possible, without the use of some type of lifting arrangement and in a very simple way, a transfer of the cuvette holder from perpendicular movement to longitudinal movement.

To assure a sufficient and uniform tensioning of the conveyor belt, the belt rolls at the longitudinal ends of the longitudinal conveyor are so positioned relative to one another on their shafts that the effective length of the conveyor belt in each angular position of the belt rolls is at least nearly constant.

The test specimen providing station serves not only for the delivery of the cuvettes for the removal of the specimens, but also for adjusting the specimens to the given concentrations, which assures uniform test conditions. In connection with this, the cuvette holders have in the inventive solution measuring openings for an optical stretch which extends perpendicular to the longitudinal direction of the holder and to the direction in which the cuvettes are inserted into the holders, with an optical measuring apparatus for measuring the quantity and the absorption capability of the cuvette content being arranged in the area of the longitudinal conveyor. As a rule, the content of the cuvettes is so chosen that the liquid specimens can still be adjusted by thinning with a physiologic table salt solution to the concentration and density desired for the measurement. This adjustment is confirmed with the help of the measuring apparatus. An amount measurement can be carried out in such way that the measuring apparatus has associated with it a lifting mechanism for lifting a cuvette inside of a cuvette holder. By suitable choice of the starting amount of specimen, the optical stretch first runs through the cuvette in air. If the cuvette is then lifted, the measuring beam at some time enters into the liquid, so that the measuring apparatus detects a steplike density change. From the measured lifting path up to this density change, and the known cuvette capacity, the volume of the liquid in the cuvette can be calculated. In connection with the measured density of the liquid, the amount of liquid required for the thinning can then be calculated.

In order in this case to again develop a simple solution, the lifting apparatus is arranged below the upper run of the two-part endless band of the longitudinal conveyor and has a lifting plunger movable into a bottom opening of the cuvette holder in order to lift up the associated cuvette with an upper stop limiting the lifting path. The lifting plunger can at the same time be part of a mixing head for mixing of the content of the cuvette. A suitable mixing head for this can, for example, be an ultrasonic mixer or an HF-mixer. The stop is preferably a spring so that it holds the cuvette in contact with the plunger and at the same time can partake of the induced movements. In this way, the specimen liquid can be mixed quickly with the liquid delivered by means of the pipetting apparatus.

BRIEF DESCRIPTION OF THE DRAWINGS

Further features and advantages of the invention will be apparent from the following description which in connection with the accompanying drawings explains the invention by way of an exemplary embodiment. The drawings are:

FIG. 6 A schematic plan view of an endless conveyor with carrier frames for the reception of measuring chamber plates.

FIG. 7 A schematic side view of the endless conveyor in the direction of the arrow A in FIG. 6.

DETAILED DESCRIPTION OF PREFERRED EMBODIMENT

Figure 1:
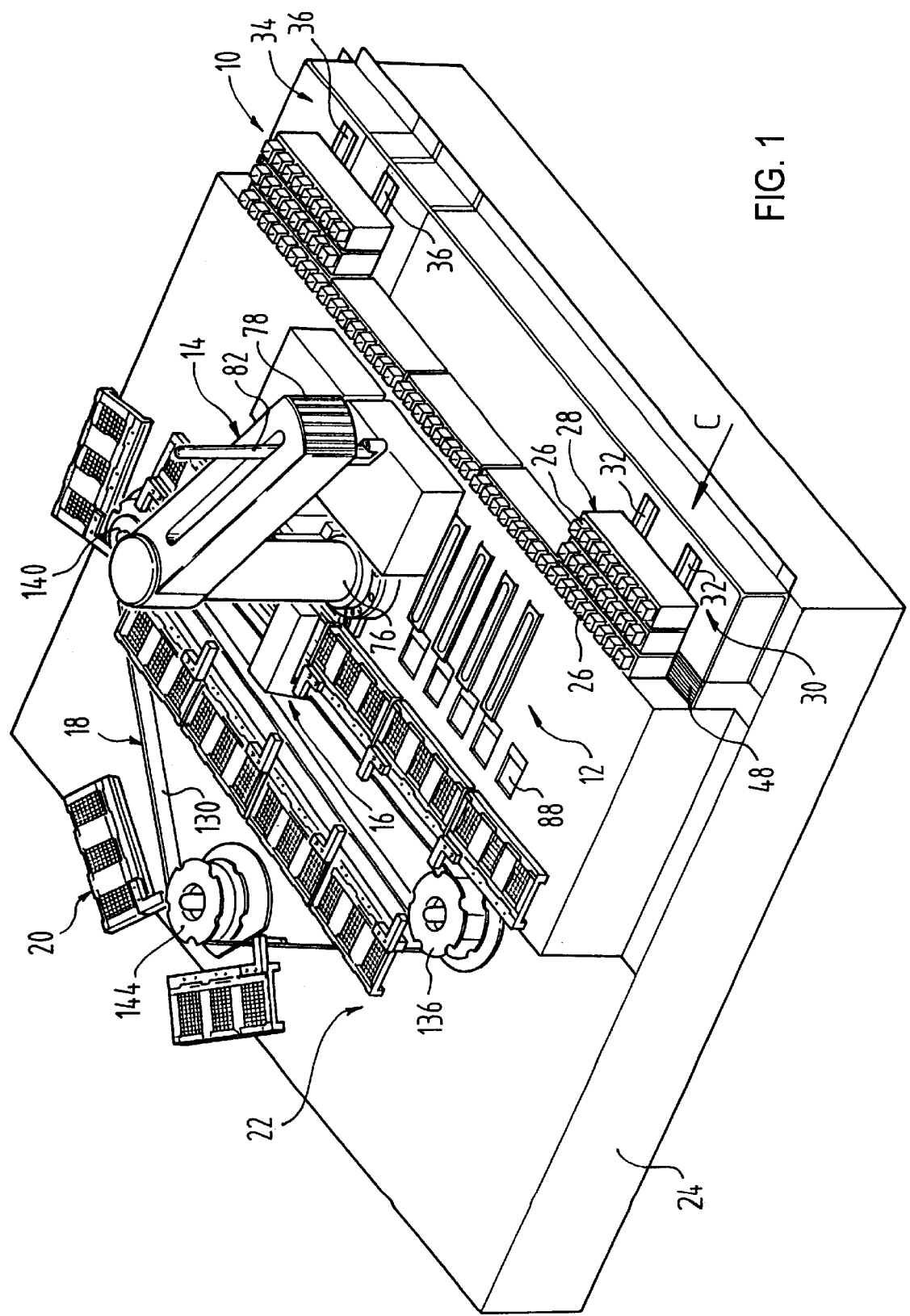
FIG. 1 A perspective schematic full view of the inventive apparatus from above.

The apparatus according to the invention illustrated in FIG. 1 includes a test specimen providing station 10 on a pedestal shaped housing, a dosing station indicated generally at 12, a pipetting apparatus 14, a measuring station 16 and an endless conveyor 18 with a plurality of carrier frames 108 for the reception of still to be described measuring chamber plates, for the purpose of transporting the measuring chamber plates through the dosing station 12, the measuring station 16 and a waiting zone 22. The illustrated apparatus is located on a pedestal shaped housing 24 which contains drive motors and control devices which are not of interest here.

The liquid specimens to be investigated are received in cuvettes 26 which stand in elongated rectangular shaped cuvette holders or cuvette racks 28. In the present example, each cuvette holder 28 receives eight cuvettes arranged in one row.

The cuvette holders 28 at a cuvette receiving location 30 are transported in the direction of the arrow C by a belt conveyor 32 to the test specimen providing station 10 and in the same way, but in the opposite direction are transported away at a cuvette take-off location 34 by means of a belt conveyor 36, with only a small section of each of the belt conveyors 32 and 36 being shown. Between the cuvette receiving location 30 and the cuvette take-off location 34, the cuvette holders 28 are moved in the longitudinal direction following one another past the pipetting apparatus 14, so that it can take specimen liquid out of the cuvettes 26. The longitudinal transport takes place with the help of a longitudinal conveyor not seen in FIG. 1 and which is explained in more detail hereinafter in connection with FIGS. 2–4. The longitudinal conveyor consists of two conveyor belts 38 parallel to one another which have a small spacing from one another (FIG. 4) and each of which is trained over a belt roll 40 in the area of the cuvette receiving location 30 and over a belt roll 42 in the area of the cuvette take-off location 34 (FIG. 3). The upper flights of the belts 38 run over a support surface 44, so as to offer a straight rigid support for the cuvette holder 28 standing on the belts 38 (FIG. 2).

Figure 2:
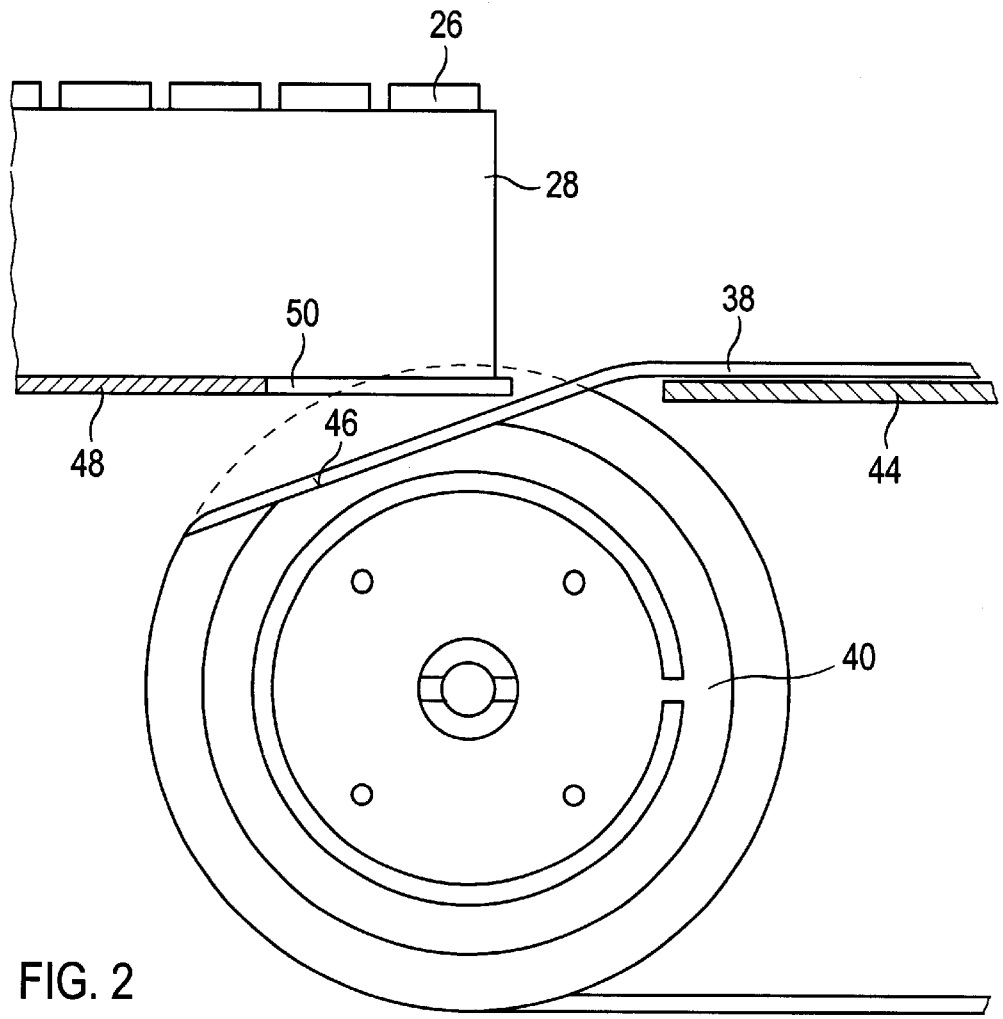
FIG. 2 A side view of an end of the longitudinal conveyor at the test specimen providing station.
Figure 3:
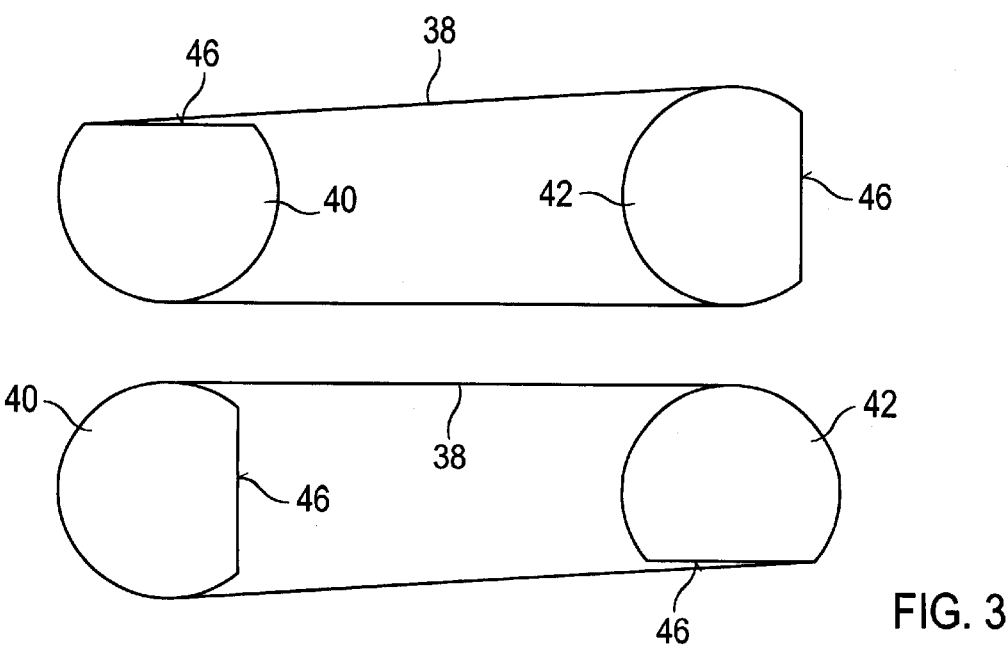
FIG. 3 A schematic illustration of the longitudinal conveyor for explaining its function.

In order to be able to transfer the cuvette holders 28 from the belt conveyor 32 to the longitudinal conveyor and from the longitudinal conveyor to the belt conveyor 36, the belt rolls 40 and 42 are each flattened along a circular secant 46, as is to be seen in FIGS. 2 and 3. The cuvette containers 28 are pushed by the belt conveyor 32 onto a supporting surface 48, having a slot 50, into which the belt rolls 40 dip with their peripheral area of full radius, as indicated by the broken circumferential line in FIG. 2. In the position illustrated in FIG. 2, the flattened section of the belt roll 40 is located directly below the support surface 48 so that the belt roll 40 does not enter the slot 50, and instead the belts 38 run below the support surface 48. In this position, a cuvette holder 28 can be pushed onto the support surface 48 without hindrance. If the belt roll 40 turns further in the clockwise direction from the position illustrated in FIG. 2, the circumferential section of full radius arrives in the slot 50 and thereby brings the belts 38 into engagement with the bottom of the cuvette holder 28 standing on the support surface 38, so that this holder will be taken up by the belts 38. At the opposite end of the longitudinal conveyor, that is at the cuvette take-off location 34, a similar arrangement runs in a reverse process, with for example, a pusher being provided for pushing cuvette holders 28 which have been unloaded onto the support surface 48 onto the belt conveyor 36, so that the cuvette holders 34 can be transported away from the apparatus.

As shown in FIG. 3, the rolls 40 and 42 are so positioned relative to one another on their axes that the associated belts 38 never run at the same time over both of the flattened sections 46 of the rolls 40 and 42. This would lead to the belt tension cyclically strongly changing between a condition in which the belt at the same time runs over both of the flattened sections and a condition in which the belt at the same time runs over the sections of full radius. To avoid this, according to FIG. 3 an arrangement is so chosen that the belt always runs on one of the rolls over a section of full radius when at the other roll it lies on and turns around the flattened section, so as to achieve an at least nearly constant belt tension. Moreover, care must be taken to see to it that the belts 38 have a sufficient elasticity so that the bands do not cyclically relax and thereby transport the cuvette holders 28 non-uniformly.

Figure 4:
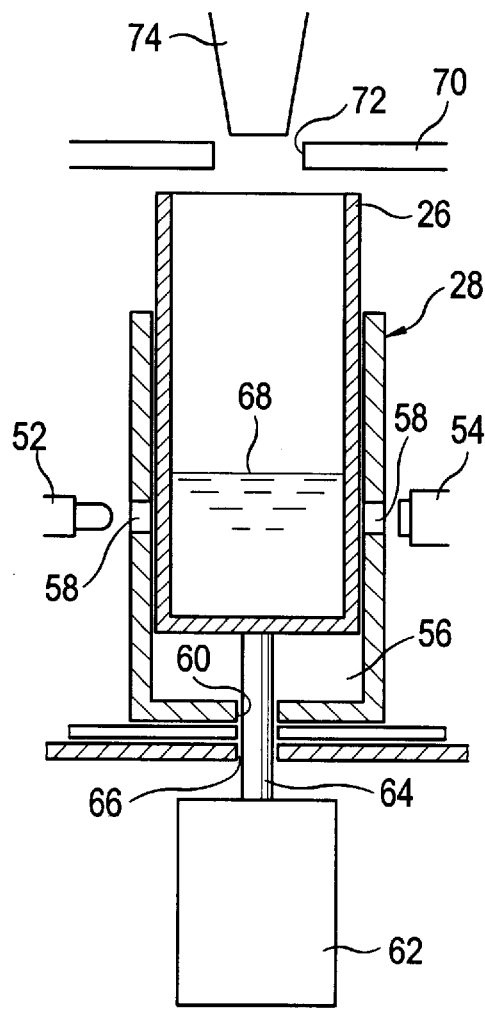
FIG. 4 A cross-sectional view through a cuvette holder located on the longitudinal conveyor in the region of the measuring apparatus provided at the test specimen preparation station.

Inside of the test specimen providing station 10 is arranged a measuring device non-illustrated in FIG. 1 so that the content of the cuvettes can be optically measured. The measuring device at the test specimen providing station is explained in more detail by way of FIG. 4. The measuring device includes an optical transmitter 52 and a receiver 54, which form a measuring stretch, which runs parallel to the support plate 44 and perpendicular to the transport direction of the longitudinal conveyor 38. To allow for the passage of the measuring beam, each cell 56 of the cuvette holder 28 for receiving a cuvette 26 has two openings 58 in its wall. In the bottom of each cell 56 of the cuvette holder 28 is further provided a passthrough opening 60. Instead of individual passthrough openings 60, a throughgoing slit can also be formed in the cuvette holder 28. Below the support plate 44 is located a lifting device 62 with a reciprocating plunger 64 which can extend through a corresponding opening 66 in the support plate 44 between the belts 38 and through the opening 60 in the holder 28 to lift up the cuvette 26 as illustrated in FIG. 4.

The cuvettes 26 are, as a rule, so filled that the fill level 68 of the cuvettes 26 standing in the holder 28 is located below the measuring stretch between the optical transmitter 52 and the receiver 54. The measuring stretch runs, therefore, through the air in the cuvette. However, if the cuvette 26 is lifted up by means of the reciprocating device 62, 64, the fluid level 68 is lifted above the measuring stretch. If one measures the lifting of the cuvette 26 up to the point at which the measuring stretch encounters the liquid, which can be determined by a change in the measuring signal, one can from this and from the known volume of the cuvette calculate the volume of liquid in the cuvette. In connection with the density of the liquid determined by the measuring apparatus, it can, therefore, be calculated in which way the test liquid is to be thinned in order to adjust it to a required standard density for the investigation.

The lifting device 62, 64 can at the same time be made as a mixing head, for example, as an ultrasonic or high frequency mixing head, to quickly achieve a dilution of the test liquid by a thorough mixing of the original liquid with the added liquid and so as to be able to control whether the desired standard requirements for the actual measurement are reached.

To enable conduction of the mixing energy to the test fluid, a good contact has to be assured between the plunger 64 and the cuvette 26. Therefore, the cuvette 26 is lifted until it engages a stop 70 which preferably is made from a spring so that upon the introduction of ultrasonic vibrations, the cuvette 26 can undertake corresponding small movements. The stop 70 has a passthrough opening 72 through which material can be filled into the cuvette 26 by a pipette 74 of the pipetting apparatus 14.

The pipetting station 14 illustrated in FIG. 1 includes a stand 76 on which is supported a pivot arm 78 for movement about a vertical axis 80. A pipette 82 is held by the arm 78 which pipette can be driven in the vertical direction and in the longitudinal direction of the pivot arm 78 and which is coupled with a suitable means by which liquid can be sucked into and dispensed from the pipette.

Figure 5:
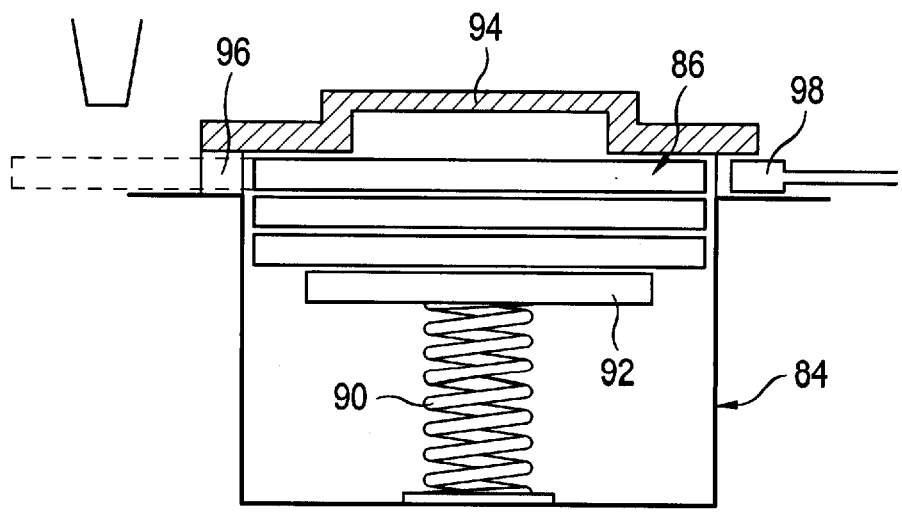
FIG. 5 A schematic section through a magazine pocket for the measuring chamber plates.

In the area of the dosing station 12, several magazine pockets 84 (FIG. 5) are located for the reception of measuring chamber plates 86, so-called microtitration plates, which are movable past an entrance opening 88. As shown in FIG. 5, a stack of such measuring chamber plates 86 are arranged in the pocket and are pressed by a spring 90 and a pressure plate 92 against a cover plate 94 covering the pocket 84. The cover plate 94 has an exit slot 96 through which the uppermost measuring chamber plate 86 can be pushed by means of a schematically indicated pusher 98.

Figure 10:
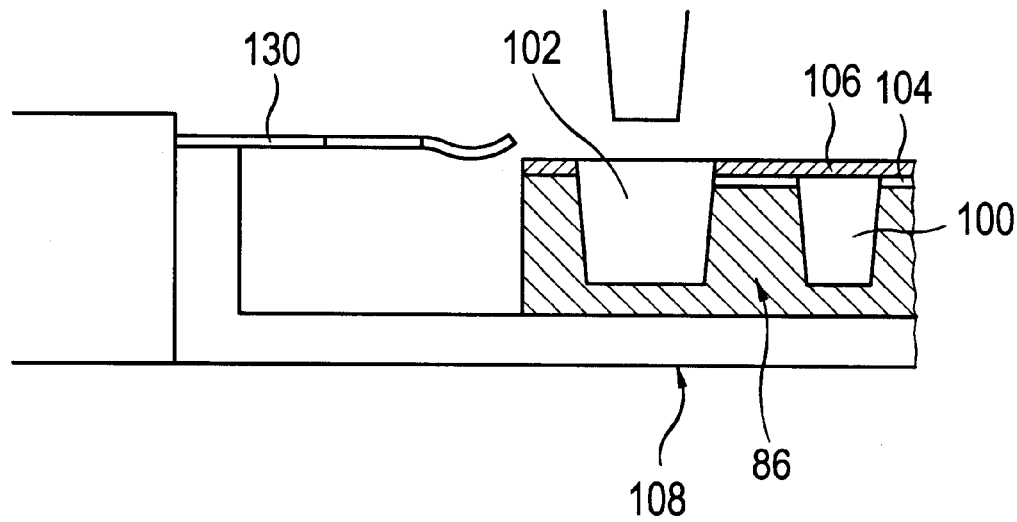
FIG. 10 A schematic detailed section through a carrier frame with a partially inserted measuring chamber plate.
Figure 11:
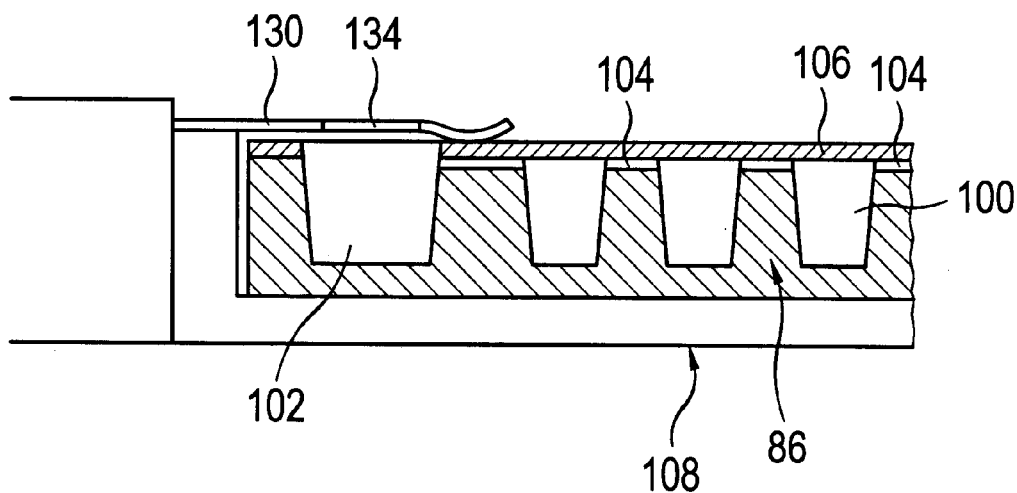
FIG. 11 A view corresponding to FIG. 10 but with the measuring chamber plate entirely inserted in the carrier frame.

In accordance with FIGS. 10 and 11, each measuring chamber plate 86 has a plurality of measuring chambers 100 arranged in the form of a matrix. Each row of measuring chambers 100 in the matrix has associated with it a filling opening 102. The filling opening 102 is connected with the measuring chambers 100 in its associated row by capillaries 104 which see to it that by capillary effect a liquid filled into the filling opening 102 reaches the individual measuring chambers 100. The manufacture of these measuring chamber plates 86 takes place in such way that a plastic plate is made with recesses corresponding to the chambers 100, 102 and the capillaries 104 which recesses subsequently are sealingly closed, except for the filling opening 102, by a cover foil 106 as is seen in FIGS. 10 and 11.

Figure 8:
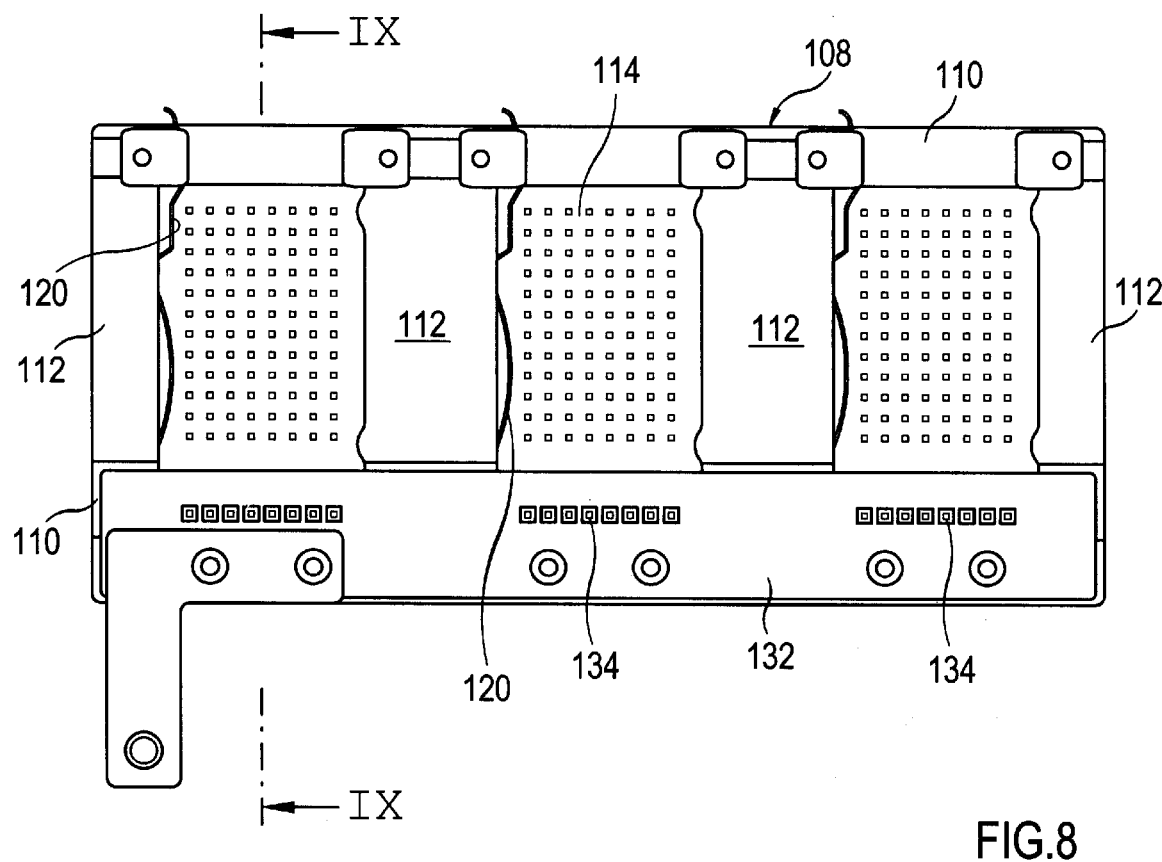
FIG. 8 A plan view of a carrier frame for the reception of measuring chamber plates.
Figure 9:
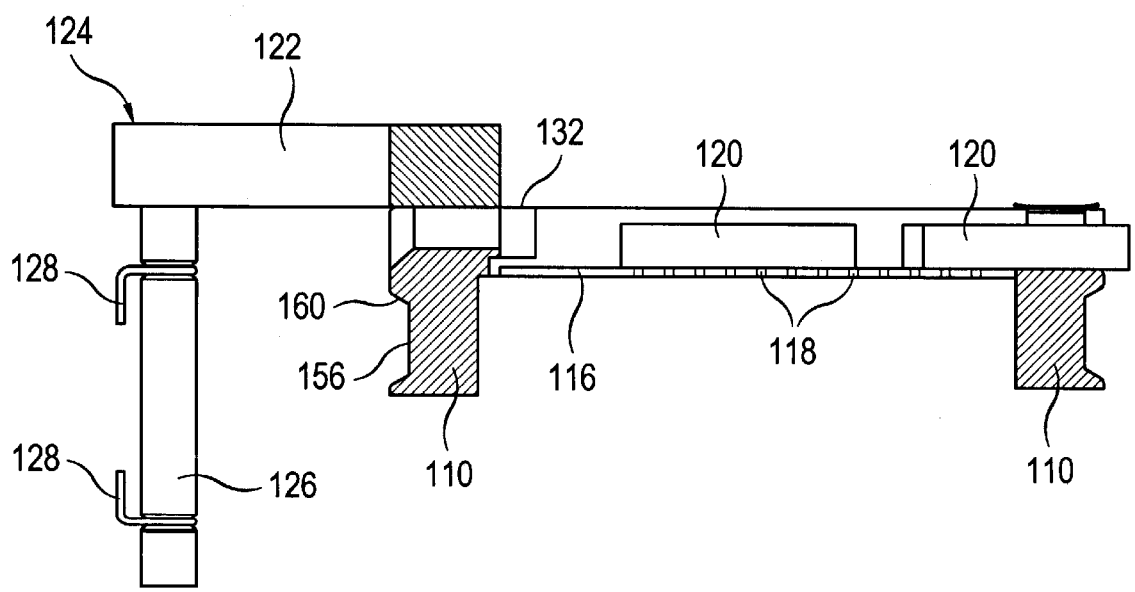
FIG. 9 A section along the line IX—IX in FIG. 8.

The measuring chamber plates 86 filled by the pipetting apparatus 14 are transferred to carrier frames 108 with the help of the pushers 98. The carrier frames 108 are connected with the endless conveyor 18 and the measuring chamber plates 86 remain in carrier frames 18 for the carrying out of the actual measurement. One such carrier frame 108 will now be explained with reference with FIGS. 8 and 9. The carrier frame 108 includes two longitudinal bars 110 and crossbars 112, between which flat receiving compartments 114 are formed each for receiving one measuring chamber plate 86. Each of the receiving compartments 114 is closed by a bottom plate 116 in which are formed through openings 118 arranged in the same raster as that of the measuring chambers 100 in the measuring plates 86 to allow for the passage of a measuring beam of the measuring apparatus at the measuring station 16, which will hereinafter be described in more detail. On inner surfaces of the cross bars 112 leaf springs 120 are arranged which push a measuring chamber plate 86 inserted into a receiving compartment 114 against an opposite cross bar 112 and thereby take care of providing a secure seating of the measuring chamber plate 86 in the receiving compartment 114. The carrier frame 108 is connected with the horizontal leg 122 of a support arm 124 whose vertical leg 126 is connected with a band or belt 130 of the endless conveyor 18 by clamps 128 (FIG. 9 in connection with FIG. 1). An elongated cover sheet 132 extends over the longitudinal bar 110 of the carrier frame 108 connected with the support arm 124, which cover sheet is preferably formed of spring steel and passes over the end regions of receiving compartments 114 near the longitudinal bar 110, as can be recognized in FIGS. 10 and 11. In the cover sheet 132 is a row of openings 134 which, upon the insertion of a measuring chamber plate 86 into a receiving compartment 114, come to lie over the filling openings 102 of the respective measuring chamber plates 86, as shown in FIG. 11.

The endless conveyor 18 serves to transport the carrier frames and the measuring chamber plates found in them through the dosing station 12, the measuring station 16, and the waiting zone 22. It also has the function of a store in which the measuring chamber plates remain during the entire, about six to eight hour duration, investigation procedure. At least the waiting zone 22, and preferably the entire apparatus is held at a temperature at which the microorganisms to be looked for in the liquid can optimally multiply. In order to be able to test as many liquid test specimens as possible during this time frame, the storage capacity of the endless conveyor must be sufficiently high, that is it must be able to transport a sufficient number of carrier frames. At the same time, the space requirement of the apparatus should not be unnecessarily expanded. For this reason, the belt 130, to which the carrier frames 108 are fastened, runs according to FIGS. 6 and 7 in two planes. The belts 130 run along the dosing station and the measuring station in a straight line between two roll pairs 136, 138 and 140, 142 and as well run over a direction changing roll 144 located outside of the connecting line between the two roller pairs. According to FIG. 7, the belt 130 runs in the direction of the arrow D from the lower roll 138 in the lower plane to the roll 142 and from this roll, runs inclinedly upwardly back to the roll 136 coaxial with the roll 138. From the roll 136, the belt 130 runs in the upper plane to the roll 140 coaxial with the roll 142 and from the roll 140 runs back to the lower plane over the inclined direction changing roll 144. In this way, the storage volume of the endless conveyor is considerably increased without essentially increasing the space requirement.

Figure 12:
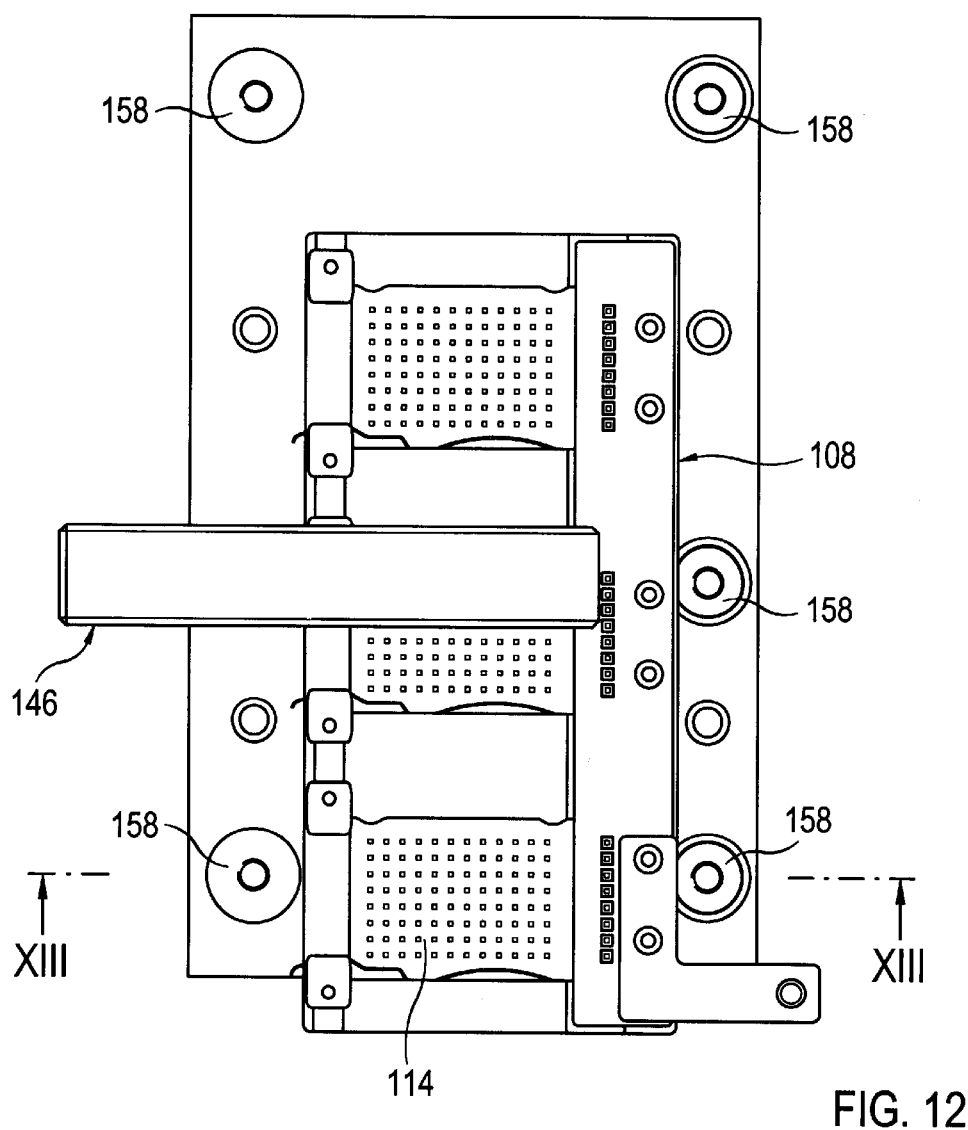
FIG. 12 A plan view of a carrier frame at the measuring station.
Figure 13:
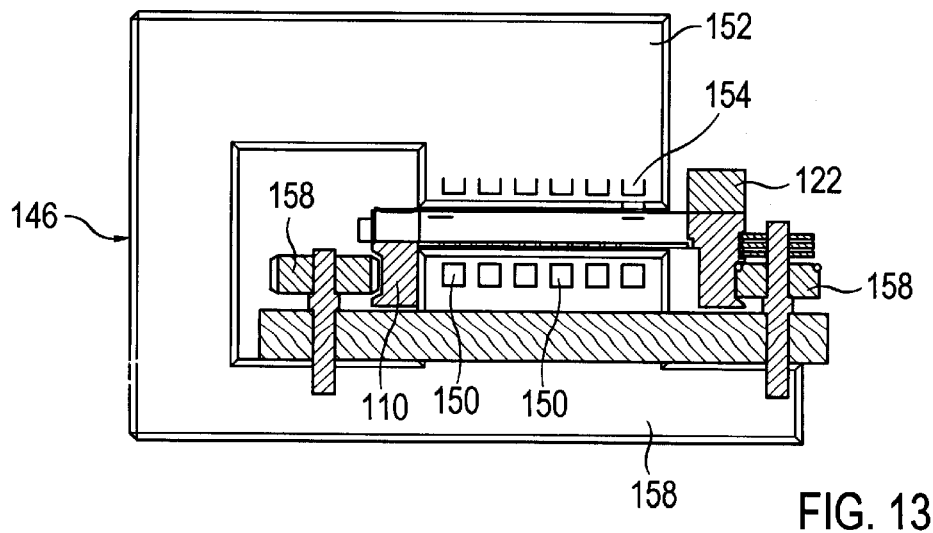
FIG. 13 A section along the line of XIII—XIII in FIG. 12.

The belt section lying between the rolls 136 and 140 runs through the measuring station 16. This includes a C-shape measuring apparatus 146 shown schematically in FIG. 13, in the lower leg 148 of which a light source, for example LEDs 150, and in the upper leg 152 of which light sensors 154 are arranged, as also given by FIG. 14. The measuring beam between the light source 150 and the light sensor 154 passes therefore through an opening 118 and the bottom 116 of a receiving compartment 114. Since these openings 118 are, like those of the measuring chambers 100, extraordinarily small, the respective carrier frames must be positioned exactly relative to the measuring device 140 at the measuring station. For this purpose, longitudinal grooves 156 are formed on the outer sides of the longitudinal bars 110 of the carrier frames 108, in which grooves corresponding portions of guide rolls 158 are received which in the area of the measuring station are arranged on both sides of the transport path for the carrier frames 108 (FIGS. 12 and 13). The guide rolls 158 on one side of the transport path are rigidly supported while on the other side, the guide rolls can be spring biased so as on one hand to assure a jolt-free insertion of the carrier frames 108 to the measuring station and on the other hand to assure an exact positioning of the carrier frames 108 at the measuring station. To stabilize the carrier frames 108 in the vertical direction at the measuring station, the grooves 156 are provided with inclined groove flanks 160 which are inclined outwardly from the groove bottom, so that the involved carrier frames 108 are centered in the vertical direction on the guide rolls 158.

The so far described apparatus operates in the following way:

After the liquid test specimens supplied in cuvettes 26 have been prepared in the above-described way for the measurement, a measuring chamber plate 86 is brought out of the magazine pocket 84 by means of the pusher 98 to a filling position illustrated in broken line in FIG. 5. By means of the pipetting apparatus 14, liquid is taken from a cuvette 26 and filled into a filling opening 102 of a measuring chamber plate 86. The filled or inoculated measuring chamber plate 86 is subsequently, with the help of the pusher 98, further pushed into the receiving compartment 14 of a carrier frame 108 which, as not seen in FIG. 1, is moved in the lower plane of the endless conveyor 18, that is between the rolls 138 and 142 past the dosing station 12. If needed, the insertion of a measuring chamber plate 86 into the carrier frame 108 may not be complete so that at a later point of time other liquid or detection chemicals can be after dosed (FIG. 10). If the measuring chamber plates 86 are completely pushed into the carrier frame 108, such after dosing can also take place through the openings 134 in the cover sheet 132, as one can recognize from FIG. 11.

Subsequently, the carrier frame moves through the waiting zone for a given amount of time, during which the microorganisms in the test specimens can multiply. When the carrier frame 108 then reaches the upper plane of the endless conveyor between the rolls 136 and 140, it is moved through the measuring station 16, in which the measuring chambers 100 are measured by row, to test whether a detectable reaction has taken place, especially whether a color change has occurred which makes it possible to identify a given microorganism. This process can be repeated several times during the time frame from six to eight hours. The measuring chamber plate need not be further manipulated during this time frame. It remains for the entire time in the carrier frame 108. Therefore, the danger of a disturbance in the running of the measurement during this time due to manipulation errors is very much lessened.

Figure 14:
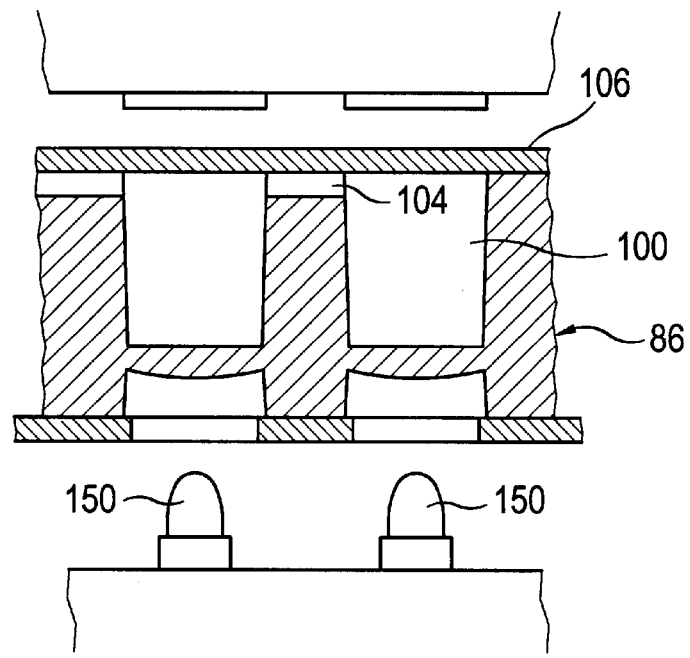
FIG. 14 A schematic partial section through a measuring chamber plate at the measuring station.

FIG. 14 shows a special form of the measuring chamber plate in which the bottom 160 is curved like a lens at the individual measuring chambers 100 in order to bundle the light emitted from the light sources 150. Therefore, even from a weak light source a sufficient measuring beam can be conducted through the measuring chamber 100. At the same time, the possibility of stray light reaching other measuring chambers or falling on other measuring sensors is reduced.

Figure 15:
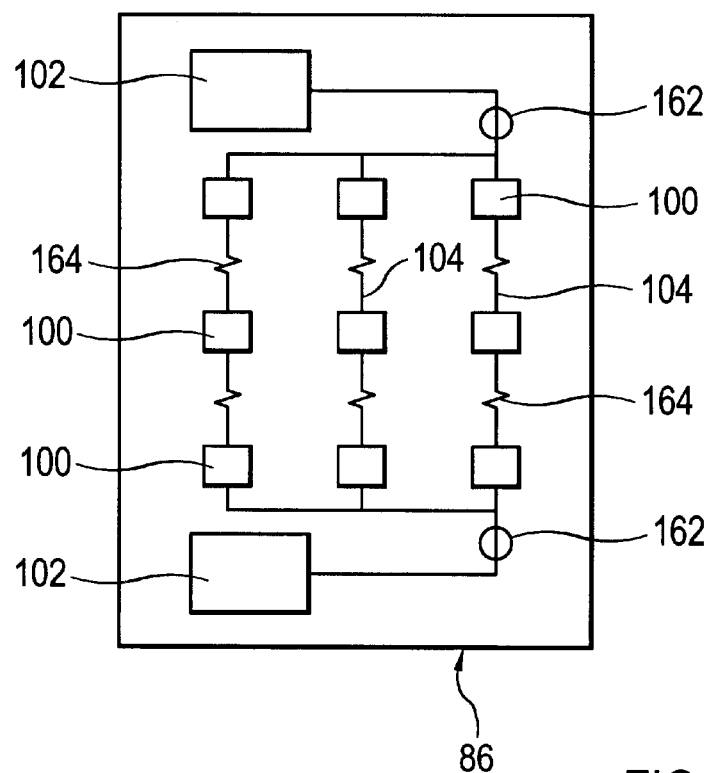
FIG. 15 A schematic plan view of an alternate implementation of a measuring chamber plate.

FIG. 15 shows in a schematic way a plan view of a special implementation of a measuring chamber plate wherein the measuring chambers 100 are again arranged in matrix form, and wherein filling openings 102 are located at both ends of the rows of measuring chambers. Downstream of each filling opening 102 is provided a spot 162 at which the capillary can be interrupted after the filling of the measuring chambers 100. This can be accomplished by a distortion of the capillary by, for example, the covering foil 106 being pressed into the capillary channel.

Between the measuring chambers 100 are provided cross sectional changes 164 at which the capillary effect is first extinguished, so that a liquid filled into the measuring chamber 100 lying next to the filling opening 102 does not automatically get drawn into the downstream lying measuring chamber. Not until the application of an external effect, for example, by means of an ultrasonic driver or the like is the capillary effect again established. In this way, it is possible by way of the capillary effect to draw into each measuring chamber 100 an amount of liquid which only partially fills the involved chamber 100.

What is claimed is:

1. An apparatus for determining microorganisms in liquid test specimens, said apparatus comprising a test specimen providing station with a transport apparatus for the continuous provision of cuvettes containing specimens to be investigated, a dosing station with a pipetting apparatus for the removal of specimens from the cuvettes and for the filling of the specimens into measuring chambers, which measuring chambers are formed in matrix arrangement in a measuring chamber plate, a measuring station with a measuring apparatus for optically measuring the specimens in the measuring chambers, and an endless conveyor for serially receiving the measuring chamber plates and for transporting the same through the dosing station, the measuring station and through a controllable temperature waiting zone.

2. An apparatus according to claim 1, wherein the endless conveyor has a plurality of carrier frames each having at least one receiving compartment for receiving a measuring chamber plate.

3. An apparatus according to claim 2, wherein the endless conveyor has an endless conveying member which is guided over rolls and onto which conveying member the carrier frames are fastened.

4. An apparatus according to claim 3, wherein the conveying member runs in at least two vertically superimposed planes.

5. An apparatus according to claim 4, wherein at least two rolls are arranged axially above one another at two locations spaced horizontally from one another and at least one further direction changing roll is provided for the conveying member, which direction changing roll is located at a location outside of the line extending between the first mentioned rolls.

6. An apparatus according to claim 3, wherein the conveying member is a toothed belt.

7. An apparatus according to claim 2, wherein at the measuring station guide means are provided for guiding the carrier frames relative to the measuring apparatus.

8. An apparatus according to claim 7 wherein the guide means include guide rolls which are arranged on both sides of the transport path of the carrier frames so that the guide rolls come into contact with side surfaces of the carrier frames running parallel to the transport direction.

9. An apparatus according to claim 8, wherein the guide rolls intended to contact one of the side surfaces are biased in the direction toward the oppositely lying guide roll.

10. An apparatus according to claim 8, wherein guide grooves running parallel to the transport direction are formed in the side surfaces of the carrier frame, which grooves are designed to receive corresponding portions of the guide rolls.

11. An apparatus according to claim 10, wherein the guide grooves and/or the guide rolls in their edge regions have a profile similar to a V.

12. An apparatus according to claim 2, wherein the receiving compartment of the carrier frame is formed as a sliding guide having an opening on a side of the carrier frame remote from the conveyor member.

13. An apparatus according to claim 2, wherein the receiving compartment has a bottom which bottom is transparent at least in the region of the measuring chambers of a measuring chamber plate inserted into the receiving compartment.

14. An apparatus according to claim 2, wherein the bottom of the receiving compartment at the places which correspond to the measuring chambers of a measuring chamber plate inserted into the receiving compartment has passthrough openings.

15. An apparatus according to claim 2, wherein at the dosing station is at least one magazine pocket for storing measuring chamber plates stacked on one another and a delivery device for delivering the uppermost measuring chamber plate from the magazine pocket (into a receiving compartment of a carrier frame moving through the dosing station.

16. An apparatus according to claim 15, wherein an upwardly biased pressure plate is arranged in the magazine pocket.

17. An apparatus according to claim 15, wherein the delivery device is so formed and controlled that it moves a measuring chamber plate out of the magazine pocket into a dosing position at which the test material is filled into the measuring chambers and subsequently moves the measuring chamber plate into the receiving compartment of a carrier frame.

18. An apparatus according to claim 15, wherein the delivery device is formed as a pusher.

19. An apparatus according to claim 2, wherein in the measuring chamber plate at least one group of measuring chambers is formed, which measuring chambers are connected with at least one filling opening and with one another by capillaries.

20. An apparatus according to claim 19, wherein the measuring chambers are arranged in rows and columns, with the measuring chambers lying in a row being connected by capillaries and the filling openings for the rows being arranged in a column.

21. An apparatus according to claim 20, wherein the column of the filling openings is arranged at an end of the measuring chamber plate with respect to the insertion direction and is arranged perpendicular to the insertion direction, and a cover is provided on the carrier frame to close the filling openings of a measuring chamber plate inserted into a receiving compartment.

22. An apparatus according to claim 20, wherein at the end of a row of connected together measuring chambers an air escape hollow space is arranged.

23. An apparatus according to claim 20, wherein in a capillary between each of two measuring chambers a cross-sectional change is so formed that automatic liquid passage by way of capillary effect is prevented, and so that liquid passage by capillary effect can be initiated by an externally originating effect exerted on the measuring chamber plate.

24. An apparatus according to claim 23, wherein at the dosing station is arranged an ultrasonic driver couplable with the measuring chamber plate.

25. An apparatus according to claim 20, wherein the measuring chambers and the capillaries are formed in the measuring chamber plate as upwardly opening recesses which are closed by a cover foil.

26. An apparatus according to claim 25, wherein the cover foil is transparent at least in the region of the measuring chambers.

27. An apparatus according to claim 20, wherein the measuring chamber plate is transparent at least in the area of the measuring chamber bottoms.

28. An apparatus according to claim 27, wherein the measuring chamber bottoms are of smaller thickness than the measuring chamber plate.

29. An apparatus according to claim 27, wherein at least one side of each measuring chamber bottom is formed as a light refracting surface, especially as a lens surface.

30. An apparatus according to claim 20, wherein each measuring chamber bottom is displaced toward the middle of the plate so that below the measuring chamber bottom a hollow space is formed.

31. An apparatus according to claim 2, wherein the measuring chamber plate is made of plastic.

32. An apparatus according to claim 1, wherein the measuring apparatus includes at least one light source and at least one light sensor associated with the light source which light source and light sensor are so arranged that a measuring beam passes through a measuring chamber perpendicular to the plane of the measuring chamber plate.

33. An apparatus according to claim 32, wherein a plurality of light source/light sensor pairs are provided which in number and arrangement correspond to the measuring chambers of at least one of the measuring chamber rows.

34. An apparatus according to claim 1, wherein the cuvettes are arranged in a row in elongated rectangular shape cuvette holders, the specimen providing station has a cuvette receiving location and a cuvette take-off location in which the cuvette holders are transported perpendicularly to their longitudinal direction and which receiving location and take-off location are connected with one another by a longitudinal conveyor by means of which the cuvette holders are transported in their longitudinal direction past the dosing station.

35. An apparatus according to claim 34, wherein the longitudinal conveyor has an endless conveying belt which at the ends of the longitudinal conveyor is guided around one belt roll each, each of which extends into a slot parallel to the belt direction of a support surface for a cuvette holder flush with the transport plane at the cuvette receiving location and at the cuvette take-off location and which at a portion of its circumference is flattened along a circular secant.

36. An apparatus according to claim 35, wherein the belt rolls, at the longitudinal ends of the longitudinal conveyor are so rotatably positioned relative to one another on their shafts that the effective length of the conveyor band in each position of the belt rolls is at least nearly constant.

37. An apparatus according to claim 34, wherein the cuvette holders have measuring openings for an optical measuring stretch which extends perpendicular to the longitudinal direction of the holder and to the insertion direction of the cuvettes in the holder, and in the area of the longitudinal conveyor an optical measuring apparatus is arranged for measuring the amount and the absorption ability of the content of the cuvette.

38. An apparatus according to claim 37, wherein the measuring apparatus has a lifting apparatus for lifting a cuvette within a cuvette holder.

39. An apparatus according to claim 38, wherein the lifting apparatus is arranged below the upper run of the two part endless belt and has a lifting plunger for extending through a bottom opening of the cuvette holder in order to bias the involved cuvette against an upper stop.

40. An apparatus according to claim 39, wherein the lifting plunger is part of a mixing head for mixing the content of the cuvette.

41. An apparatus according to claim 40, wherein the mixing head is an ultrasonic mixer.

42. An apparatus according to claim 40, wherein the mixing head is an HF-mixer.

43. An apparatus according to claim 39, wherein the stop has a passthrough opening providing access to the cuvette opening.

44. An apparatus according to claim 40, wherein the stop is formed by a spring.

* * * * *